United States Patent [19]

Ward et al.

[11] Patent Number: 5,541,310

[45] Date of Patent: Jul. 30, 1996

[54] HERBICIDE RESISTANT PLANTS

[75] Inventors: Eric R. Ward; Sandra Volrath, both of Durham, N.C.; Shinichi Koizumi, Nishinomiya, Japan; Sachiyo Tada, Osaka, Japan; Ichiro Mori, Hyogo, Japan; Genji Iwasaki, Hyogo, Japan

[73] Assignee: Ciba-Geigy Corporation, Tarrytown, N.Y.

[21] Appl. No.: 236,427

[22] Filed: Apr. 29, 1994

Related U.S. Application Data

[63] Continuation-in-part of Ser. No. 61,644, May 13, 1993, abandoned.

[51] Int. Cl.⁶ .............................. C12N 5/10; C12N 15/63; C12N 15/29
[52] U.S. Cl. ............... 536/23.6; 435/240.2; 435/240.4; 435/252.3; 435/320.1
[58] Field of Search .................................. 800/205, 255, 800/DIG. 26, DIG. 56, DIG. 58; 435/69.1, 172.3, 172.1, 320.1, 240.4, 240.49, 240.2, 252.3; 536/24.1, 23.6

[56] References Cited

U.S. PATENT DOCUMENTS

| | | | |
|---|---|---|---|
| 4,761,373 | 8/1988 | Anderson et al. | 435/172.3 |
| 4,975,374 | 12/1990 | Goodman et al. | 435/172.3 |
| 5,013,659 | 5/1991 | Bedbrook et al. | 435/172.3 |
| 5,162,602 | 11/1992 | Somers et al. | 800/235 |

FOREIGN PATENT DOCUMENTS

476502A2  4/1992  European Pat. Off. .

OTHER PUBLICATIONS

Kishore et al (1988) Ann. Rev. Biochem. 57:627–663.

Mazur et al (1989) Ann. Rev. Plant Physiol Plant Mol Biol 40:441–470.

Ames, B. N., "The Biosynthesis of Histidine: D-erythro–Imidazole–Glycerol Phosphate Dehydrase", *J. Biol. Chem.*, 228:131–143 (1957).

Ames, B. N. et. al., "The Biosynthesis of Histidine, Imidazoleglycerol Phosphate, Imidazoleacetol Phosphate, and Histididnol Phosphate", *J. Biol. Chem.*, 212:687–697 (1955).

DasSarma, S., et al., "Plant Glutamine Synthetase Complements a glnA Mutation in *Escherichia coli*", *Science*, 232:1242–1244 (1986).

Fani, R., et al., "Cloning of Histidine Genes of *Azospirillum brasilense*: Organization of the ABFH Gene Cluster and Nucleotide Sequence of the hisB Gene", *Mol. Gen. Genet.*, 216:224–229 (1989).

Goldman, G. H., et al., "Molecular Cloning of the Imidazoleglycerolphosphate Dehydratase Gene of *Trichoderma harzianum* by Genetic Complementation in *Saccharomyces cerevisiae* Using a Direct Expression Vector", *Mol. Gen. Genet.*, 234:481–488 (1992).

Heim. D. R., et al., "Primary Site of Action of Amitrole in *Arabidopsis thaliana* Involves Inhibition of Root Elongation but Not of Histidine or Pigment Biosynthesis", *Plant Physiol.*, 91:1226–1231 (1989).

Minet, M., et al., "Complementation of *Saccharomyces cerevisiae* Auxotrophic Mutants by *Arabidopsis thaliana* cDNAs", *The Plant Journal*, 2(3):417–422 (1992).

Smith, J. K., et al., "Functional Expression of Plant Acetolactate Synthase Genes in *Escherichia coli*", *Proc. Natl. Acad. Sci.*, 86:4179–4183 (1989).

Glaser et al., "Subunit Structure and Photooxidation of Yeast Imidazoleglycerolphosphate Dehydratase", *Biochemistry*, 13(24): 5145–5152 (1974).

Mano et al., "Purification and Properties of a Monofunctional Imidazoleglycerol–Phosphate Dehydratase from Wheat", *Plant Physiol.*, 103: 733–739 (1993).

Wiater et al., "Histidine biosynthesis and its regulation in higher plants", *Chemical Abstracts*, 76:182 (1972).

Wiater et al., "Synergistic inhibition of plant imidazoleglycerol phosphate dehydratase by aminotriazole and phosphate", *Chemical Abstracts*, 76: 126 (1972).

Wiater et al., "Structural requirements for inhibition of yeast imidazoleglycerolphosphate dehydratase by triazole and anion inhibitors", *Biological Abstracts*, 58(8): 4508(1972).

EMBL Sequence Database Rel 38, Acc No U02689 (Jan. 1, 1994).

EMBL Sequence Database Rel 38, Acc No U02690 (Jan. 1, 1994).

*Primary Examiner*—David T. Fox
*Assistant Examiner*—Elizabeth McElwain
*Attorney, Agent, or Firm*—James Scott Elmer

[57] ABSTRACT

Disclosed are plants, plant tissue and plant seed, whose growth and development are tolerant of, or resistant to various imidazole and triazole herbicidal compounds, at levels which normally are inhibitory to the plants. The tolerance or resistance is conferred by an altered imidazoleglycerol phosphate dehydratase (IGPD). Plant genes encoding wild-type and altered IGPD, purified plant IGPD, methods of isolating IGPD from plants, and methods of using both purified IGPD and IGPD-encoding genes are also disclosed.

10 Claims, No Drawings

HERBICIDE RESISTANT PLANTS

CROSS-REFERENCE TO RELATED APPLICATIONS

This application is a continuation-in-part of U.S. Ser. No. 08/061,644 filed May 13, 1993, now abandoned, which disclosures are herein incorporated in their entirety.

FIELD OF THE INVENTION

The invention relates generally to agricultural biotechnology. More specifically, it relates to herbicide resistance in plants, plant tissues and seeds.

BACKGROUND OF THE INVENTION

The use of herbicides to control weeds or plants in crops has become almost a tmiversal practice. The relevant market exceeds a billion dollars annually. Despite this extensive use, weed control remains a significant and costly problem for farmers.

Effective use of herbicides requires sound management. For instance, time and method of application and stage of weed plant development are critical to getting good weed control with herbicides. Since various weed species are resistant to herbicides, the production of effective herbicides becomes increasingly important.

Unfortunately, herbicides that exhibit greater potency, broader weed spectrum and more rapid degradation in soil also have greater crop phytotoxicity. Crop hybrids or varieties resistant to the herbicides would allow for the use of the herbicides without attendant risk of damage to the crop. U.S. Pat. No. 4,761,373 to Anderson et al. is directed to plants resistant to various imidazolinone or sulfonamide herbicides. The resistance is conferred by an altered acetohydroxyacid synthase (AHAS) enzyme. U.S. Pat. No. 4,975,374 to Goodman et al. relates to plant cells and plants containing a gene encoding a mutant glutamine synthetase (GS) resistant to inhibition by herbicides that were known to inhibit GS, e.g. phosphinothricin and methione sulfoximine. U.S. Pat. No. 5,013,659 to Bedbrook et al. is directed to plants that express a mutant acetolactate synthase which renders the plants resistant to inhibition by sulfonylurea herbicides. U.S. Pat. No. 5,162,602 to Somers et al. discloses plants tolerant to inhibition by cyclohexanedione and aryloxyphenoxypropanoie add herbicides. The tolerance is conferred by an altered acetyl coenzyme A carboxylase(ACCase).

To genetically engineer plants for the purpose of herbicide resistance, the target of the herbicide first must be identified. This task can be very difficult. For example, the genome of *E. coli* is capable of expressing at least 60 amino acid biosynthetie enzymes. Plants are much more complex, and thus contain many more enzymes. The sheer number of potential targets, therefore, is a factor. Also, plant enzymes have proven difficult to purify, which hinders large-scale in vitro screening efforts. Further, the effect of a herbicide on a particular plant enzyme cannot necessarily be predicted on the basis of the effect of the herbicide on the microbial analogue. Various herbicides, e.g. aminotriazoles, affect different biosynthetie pathways in plants and microbes. See, Hilton et al., Arch. Biochem. Biophys. 112:544–547 (1965); Jeim and Larrinua, Plant Physiol. 91:1226–1231 (1989). Finally, plants have other resistance mechanisms such as rapid metabolism, and poor uptake and translocation of the herbicide which complicates elucidation of the enzyme target.

SUMMARY OF THE INVENTION

Applicants have purified imidazoleglycerol phosphate dehydratase (IGPD) from a plant, and have discovered that it is sensitive to various herbicies. They also have isolated cDNAs from plants which encode IGPD.

In accordance with these discoveries, the present invention provides plants, plant tissues and plant seeds resistant to inhibition by an imidazole or triazole herbicide, wherein the resistance is conferred by an altered IGPD resistant to inhibition by the herbicide at levels which normally are inhibitory to the activity of IGPD in natively expressed amounts. Plants encompassed by the invention include those which would be potential targets for the herbicides, particularly agronomically important crops such as maize and other cereal crops such as wheat, oats, rye, sorghum, flee, barley, millet, turf and forage grasses, and the like, as well as cotton, sugar cane and soybeans.

The present invention is directed further to methods for the production of plants, plant tissues, and plant seeds which contain an IGPD enzyme resistant to, or tolerant of inhibition by an imidazole or triazole herbicide at a concentration which normally inhibits the activity of IGPD in natively expressed amounts. One particular embodiment of the invention is directed to the preparation of transgenie maize plants, maize tissue or maize seed which have been stably transformed with a recombinant DNA molecule comprising a suitable promoter functional in plants operably linked to a structural gene encoding wild-type IGPD. This results in over-expression of the the wild-type IGPD in the maize plant sufficient to overcome inhibition of the enzyme by the herbicide.

The present invention also embodies the production of plants which express an altered IGPD enzyme tolerant of inhibition by an imidazole or triazole herbicide at a concentration which normally inhibits the activity of wild-type, unaltered IGPD. In this embodiment, the plant may be stably transformed with a recombinant DNA molecule comprising a structural gene encoding the resistant IGPD, or prepared by direct selection techniques whereby herbicide resistant lines are isolated, characterized and developed.

The present invention is also directed to processes for making and using IGPD. In particular, the present invention provides methods of using purified, wild-type IGPD to screen for novel herbicides which affect the activity of IGPD, and to identify herbicide-resistant IGPD mutants. Genes encoding altered IGPD can be used as selectable markers in plant cell transformation methods.

DETAILED DESCRIPTION OF THE INVENTION

The present invention is directed to plants, plant tissue and plant seeds tolerant to imidazole and triazole herbicides, wherein the tolerance is conferred by an altered IGPD enzyme. IGPD[EC 4.2.1.19] catalyzes the dehydration of imidazoleglycerol phosphate (IGP) to imidazoleacetol phosphate (IAP). This reaction occurs in the histidine biosynthetic pathway. Representative plants include any plants to which these herbicides are applied for their normally intended purpose. Preferred are agronomieally important crops such as cotton, soya, rape, maize, flee, wheat, barley, oats, rye, sorghum, millet tuff, forage grasses and the like.

The term "imidazole herbicide" encompasses the imidazole represented by formula I, below, and any derivatives of formula I that exhibit herbicidal activity; that is, they inhibit the growth, metabolism or replication of plant cells or whole plants.

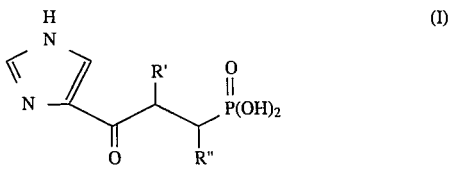

wherein R' represents hydrogen, a halogen which preferably is flourine, or an —O—L group wherein L represents hydrogen,

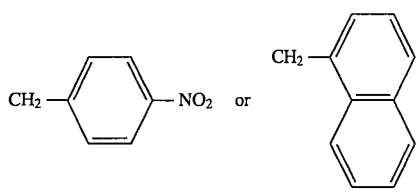

and R" represents a —SCH$_2$CH$_3$ or a SCH$_2$CH$_2$OH group. The term "triazole herbicide" encompasses herbicidal chemical compounds represented by formula II, below, and derivatives thereof which exhibit herbicidal activity as defined above.

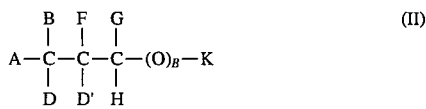

wherein A is a substiment group represented by:

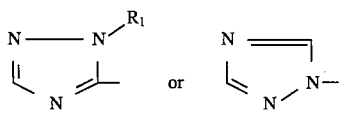

, where R$_1$ is hydrogen, C$_1$–C$_4$ alkyl or C$_2$–C$_4$ alkenyl;

B is hydrogen, C$_1$–C$_4$ alkyl or —CH$_2$OH;

D and D' independently represent hydrogen or hydroxy, with the proviso that only one of D and D' is hydroxy;

F and G independently represent C$_1$–C$_4$ alkyl;

or wherein B and G together represent —(CH$_3$)—;

n is 0 or 1; and

K is P(O)(OR$_2$)$_2$, wherein R$_2$ represents hydrogen or an alkali metal, alkaline earth metal, ammonium or an organic ammonium cation.

Levels of imidazole and triazole herbicide which normally are inhibitory to the activity of IGPD include application rates known in the art, and which depend partly on external factors such as environment, time and method of application. For example, in the case of the triazole herbicides represented by formulae (II), the application rates range from 0.0001 to 10 kg/ha, preferably from 0.005 to 2 kg/ha. This dosage rate or concentration of herbicide may be different, depending on the desired action, and can be determined by methods known in the art.

By "altered IGPD enzyme", it is meant increased expression of wild-type, herbicide-sensitive enzyme, or expression of a mutant, herbicide-tolerant IGPD. The "increased expression" results in a level of IGPD in the plant cell at least sufficient to overcome growth inhibition caused by the herbicide. The level of expressed IGPD generally is at least two times, preferably five times, and more preferably at least ten times the natively expressed amount. Thus, increased expression may be due to multiple copies of a wild-type IGPD gene; multiple occurrences of the IGPD coding sequence within the IGPD gene, i.e. gene amplification; or a mutation in the non-coding, regulatory sequence of the endogenous IGPD gene in the plant cell. Plants containing such altered IGPD enzyme can be obtained by direct selection. This method is known in the art. See, e.g. Somers et al. in U.S. Pat. No. 5,162,602, and Anderson et al. in U.S. Pat. No. 4,761,373, and references cited therein. These plants also may be obtained via genetic engineering techniques known in the art.

Increased expression of herbicide-sensitive IGPD also can be accomplished by stably transforming a plant cell with a recombinant or chimerio DNA molecule comprising a promoter capable of driving expression of an associated structural gene in a plant cell, linked to a homologous or heterologous structural gene encoding IGPD. By "homologous," it is meant that the IGPD gene is isolated from an organism taxonomically identical to the target plant cell. By "heterologous," it is meant that the IGPD gene is obtained from an organism taxonomically distinct from the target plant cell. IGPD genes can be obtained by complementing a bacterial or yeast auxo.trophic mutant with a plant cDNA library. See, e.g. Snustad et al, Genetics 120;1111–1114 (1988) (maize glutamine synthase); Delauney et al., Mol. Genet. 221:299–305 (1990) (soybean-pyrroline-5-carboxylate reductase); Frisch et al., Mol. Gen. Genet. 228:287–293(1991) (maize dihydrodipicolinate synthase); Eller et al., Plant Mol. Biol. 18:557–566 (1992) (rape chloroplast 3-isopropylmalate dehydrogenase); Proc. Natl. Acad. Sci, USA 88:1731–1735 (1991); Minet et al., Plant J. 2:417–422 (1992) (dihydroorotate dehydrogenase) and references cited therein. Other known methods include screening genomic or cDNA libraries of higher plants, for example, for sequences that cross-hybridize with specific nucleic acid probes, or by screening expression libraries for the production of IGPD enzymes that cross-react with specific antibody probes. A preferred method involves complementing an *E. coli* his B auxotrophic mutant with an *Arabidopsis thaliana* cDNA library.

The term "altered IGPD enzyme" as used herein also encompasses herbicide-tolerant IGPD. Genes encoding such enzymes can be obtained by numerous strategies known in the art. A first general strategy involves direct or indirect mutagenesis procedures on microbes or tissue cultures of all types, seeds or plants. For instance, a genetically manipulable microbe, e.g. *E. coli* or *S. cerevisiae*, may be subjected to random mutagenesis in vivO, with, for example UV light or ethyl or methyl methane sulfonate. Mutagenesis procedures are described, for example in Miller, *Experiments in Molecular Genetics,* Cold Spring Harbor Laboratory, Cold Spring Harbor, N.Y. (1972); Davis et al., *Advanced Bacterial Genetics,* Cold Spring Harbor Laboratory, Cold Spring Harbor, N.Y. (1980); and Sherman et al., *Methods in Yeast Genetics,* Cold Spring Harbor Laboratory, Cold Spring Harbor, N.Y. (1983). The microbe selected for mutagenesis contains an IGPD gene, the sequence of which is known. The mutagenized cells are grown in the presence of normally inhibitory concentrations of the inhibitor. DNA is prepared from colonies that display resistance to the inhibitor; the IGPD genes from these colonies are isolated, either by cloning or by polymerase chain reaction amplification, and their sequences determined. Putatively mutant IGPD genes are tested for their ability to confer inhibitor resistance on wild-type cells upon transformation.

A second method of obtaining mutant herbicide-resistant alleles of IGPD involves direct selection in plants. For example, the effect of an IGPD inhibitor such those as described above, on the growth inhibition of plants such as Arabidopsis, may be determined by plating seeds sterilized by art-recognized methods on plates on a simple minimal salts medium containing increasing concentrations of the inhibitor. Such concentrations are in the range of 1, 3, 10, 30, 110, 330, 1000 and 3300 parts per million (ppm). The lowest dose at which significant growth inhibition can be reproducibly detected is used for subsequent experiments.

Ethyl methane sulfonate (EMS) mutagenized $M_2$ seeds (Lehle Seeds, Tucson, Ariz.), i.e. progeny seeds of plants grown from seeds mutagenized with ethyl methane sulfonate, are plated at densities of up to 10,000 seeds/plate (10 cm diameter) on minimal salts medium containing an appropriate concentration of inhibitor to select for resistance. Seedlings that continue to grow and remain green 7–21 days after plating are transplanted to soil and grown to maturity and seed set. Progeny of these seeds are tested for resistance to the herbicide. Assuming the resistance is dominant, plants whose seed segregate 3:1::resistant:sensitive are presumed to have been heterozygous for the resistance at the $M_2$ generation. Plants that give rise to all resistant seed are presumed to have been homozygous for the resistance at the $M_2$ generation.

Two approaches can be taken to confirm that the genetic basis of the resistance is an altered IGPD gene. First, given the sequence of the Arabidopsis cDNA shown in Table 1 (SEQ ID NO:1) below, new alleles of the IGPD gene that putatively result in resistance to the inhibitor can be isolated using PCR. After sequencing the alleles to determine the presence of mutations in the coding sequence, the alleles can be tested for their ability to confer resistance to the inhibitor on plants into which the putative resistance-conferring alleles have been transformed. These plants can be either Arabidopsis plants or any other plant whose growth is susceptible to the inhibitors. Second, the IGPD genes can be mapped relative to known restriction fragment length polymorphisms (RFLPs). See, for example, Chang et al. Proc. Natl. Acad, Sci, USA 85:6856–6860 (1988); Nam et al., Plant Cell 1:699–705 (1989). The resistance trait can be independently mapped using the same markers. If the resistance maps to a position indistinguishable from one of the IGPD gene's position, it is likely the result of a mutation in that IGPD gene.

A third method of obtaining inhibitor-resistant alleles of lGPD is by selection in plant cell cultures. Actively growing callus or suspension cultures of a plant of interest are grown on defined medium lacking histidine in the presence of increasing concentrations of the inhibitor. Varying degrees of growth are recorded in different cultures. In certain cultures, fast-growing variant colonies arise that continue to grow even in the presence of normally inhibitory concentrations of inhibitor. Putative resistance-conferring alleles of the lGPD gene are isolated and tested as described in the foregoing paragraphs.

A fourth method involves mutagenesis of wild-type, herbicide sensitive IGPD genes in bacteria or yeast, followed by culturing the microbe on medium that lacks histidine, but which contains inhibitory concentrations of the inhibitor, and then selecting those colonies that grow in the presence of the inhibitor. More specifically, a plant cDNA, such as the Arabidopsis cDNA encoding IGPD is cloned into a microbe that otherwise lacks IGPD activity. Examples of such microbes include *E. Coli* or *S. cerevisiae* auxotrophic mutants. The transformed microbe is then subjected to in vivo mutagenesis such as described immediately above, or to in vitro mutagenesis by any of several chemical or enzymatic methods known in the art, e.g. sodium bisulfite (Shortle et al., Methods Enzymol. 100:457–468 (1983); methoxylamine (Kadonaga et al., Nucleic Acids Res. 13:1733–1745 (1985); oligonucleotide-directed saturation mutagenesis (Hutchinson et al., Proc. Natl. Acad. Sci. USA, 83:710–714 (1986); or various polymerase raisincorporation strategies (see, e.g. Shortle et al., Proc. Natl. Acad. Sci. USA, 79:1588–1592 (1982); Shiraishi et al., Gene 64:313–319 (1988); and Leung et al., Technique 1:11–15 (1989). Colonies that grow in the presence of normally inhibitory concentrations of inhibitor are picked and purified by repeated restreaking. Their plasmids are purified and tested for the ability to confer resistance to the inhibitor by retransforming them into the IGPD-lacking microbe. The DNA sequences of IGPD cDNA inserts from plasmids that pass this test are then determined.

Examples of promoters capable of functioning in plants or plant cells, i.e., those capable of driving expression of the associated structural genes such as IGPD in plant cells, include the cauliflower mosaic virus (CaMV) 19S or 35S promoters and CaMV double promoters; nopaline synthase promoters; pathogenesis-related (PR) protein promoters; small subunit of ribulose bisphosphate carboxylase (ssu-RUBISCO) promoters, and the like. Preferred are the 35S promoter and an enhanced or double 35S promoter such as that described in Kay et al., Science 236:1299–1302 (1987), incorporated herein by reference in its entirety for its relevant teachings, and the double 35S promoter cloned into pCGN2113, deposited as ATCC 40587, which are disclosed in each of commonly owned copending application serial number 07/580,43 1, filed Sep. 7, 1990, which is a continuation-in-part of Ser. No. 07/425,504, filed Oct. 20, 1989, which is a continuation-in-part of Ser. No. 07/368,672, filed June 20, 1989, which is a continuation-in-part of Ser. No. 07/329,018, filed Mar. 24, 1989, the relevant disclosures of which are herein incorporated by reference in their entirety. The promoters themselves may be modified to manipulate promoter strength to increase IGPD expression, in accordance with art-recognized procedures.

The chimerio DNA construct(s) of the invention may contain multiple copies of a promoter or multiple copies of the IGPD structural genes. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to hygromycin, kanamycin, G418, gentamycin, lincomycin, methotrexate, glyphosate, phosphinothricin, or the like. These markers can be used to select cells transformed with the chimefie DNA constructs of the invention from untransformed cells. Other useful markers are peptidic enzymes which can be easily detected by a visible reaction, for example a color reaction, for example luciferase, β-glucuronidase, or β-galactosidase.

Signal or transit peptides provide the IGPD formed on expression of the chimeric DNA constructs of the invention with the ability to be transported to the desired site of action. Examples of signal peptides include those natively linked to the plant pathogenesis-related proteins, e.g. PR-1, PR-2, and the like. See, e.g., Payne et al., Plant Mol. Biol. 11:89–94

(1988). Examples of transit peptides include the chloroplast transit peptides such as those described in Von Heijne et al., Plant Mol. Biol. Rep. 9:104–126 (1991), and mitochondrial transit peptides such as those described in Boutry et al., Nature 328:340,342 (1987). Also included are sequences that result in localization of the encoded protein to various cellular compartments such as the vacuole. See, for example, Neuhaus et al., Proc. Natl. Acad. Sci. USA 88:10362–10366 (1991) and Chrispeels, Ann. Rev. Plant Physiol. Plant Mol. Biol. 4–2:21–53 (1991). The relevant disclosures of these publications are incorporated herein by reference in their entirety.

The recombinant DNA molecules can be introduced into the plant cell in a number of art-recognized ways. Those skilled in the an will appreciate that the choice of method might depend on the type of plant, i.e. monocot or dicot, targeted for transformation. Suitable methods of transforming plant cells include microinjection (Crossway et al., BioTechniques 4:320–334 (1986)), electroporation (Riggs et al, Proc. Natl. Acad. Sci. USA 83:5602–5606 (1986), Agobacterium mediated transformation (Hinchee et al., Biotechnology 6:915–921 (1988)), direct gene transfer (Paszkowski et al., EMBO J. 3:2717–2722 (1984)), and ballistic particle acceleration using devices available from Agracetus, Inc., Madison, Wisconsin and Dupont, Inc., Wilmington, Delaware (see, for example, Sanford et al., U.S. Pat. No. 4,945, 050; and McCabe et al., Biotechnology 6:923–926 (1988)). Also see, Weissinger et al., Annual Rev. Genet. 22:421–477 (1988); Sanford et al., Particulate Science and Technology 5:27–37 91987)(onion); Christou et al., Plant Physiol. 87:671–674 (1988)(soybean); McCabe et al., Bio/Technology 6:923–926 (1988)(soybean); Datta et al., Bio/Technology 8:736–740 (1990)(rice); Klein et al., Proc. Natl. Acad. Sci. USA, 85:4305–4309 (1988)(maize); Klein et al., Bio/Technology 6:559–563 (1988)(maize); Klein et al., Plant Physiol. 91:440–444 (1988)(maize); Fromm et al., Bio/Technology 8:833–839 (1990); and Gordon-Kamm et al., Plant Cell 2:603–618 (1990)(maize); Svab et al. Proc. Natl. Acad. Sci. USA 87:8526–8530 (1990) (tobacco chloroplast).

Genes encoding altered IGPD resistant to an IGPD inhibitor can be used as selectable markers in plant cell transformation methods. For example, plants, plant tissues or plant cells can be co-transformed with a transgene of interest and a gene encoding an altered IGPD capable of being expressed in the plant as a selectable marker. The thus-transformed cells are transferred to medium containing the IGPD inhibitor wherein only the transformed cells will survive. The method is applicable to any plant cell capable of being transformed with an altered IGPD-encoding gene, and can be used with any transgene of interest, although the method does not require use of the transgene. Expression of the transgene and the IGPD gene can be driven by the same promoter functional on plant cells, or by separate promoters.

Another embodiment of the present invention is directed to purified plant IGPD, per se. IGPD can be prepared by isolating crude IGPD from plant material and then purifying the thus obtained extract. The purification of plant enzymes from plant material has been difficult, primarily due to the low amounts of the enzymes in plants. In the case of IGPD, the situation was exacerbated since standard assays used in previous studies were unreliable. Thus, in many plants, IGPD activity was undetectable. Specifically, the direct determination of enolized IAP (imidazoleacetol phosphate) in strong alkali at 280 nm, described in Ames, J. Biol. Chem. 228:13 1–143 (1957) and which was used in all previously reported studies, was not applicable in crude plant extracts and slightly enriched enzyme preparations due to a high background absorbance inherent to such plant preparations. The present inventors have discovered that an alternative method which involves measuring the amount of imidazoleacetol (IA) produced from the enzymatic hydrolysis of synthetic IAP in the presence of alkaline phosphatase and alkali, rather than HCl, by determining the absorption of its enolized form in alkali at 370 nm, provides a more sensitive method adequate to detect previously undetectable IGPD in plants.

The starting material, e.g. crude enzyme extract, can be prepared in accordance with known techniques. Likewise, purification of the crude IGPD extract can be accomplished by art-recognized procedures. See, Scopes, *Protein Purification; Principles and Practice*, 2nd Ed., Springer-Verlag (New York, 1987). In general, a combination of purification techniques such as fractionation and chromatography is required to obtain pure IGPD. By "pure," it is meant a substantially homogeneous IGPD preparation. Preferred purification schemes are combinations of techniques such as ammonium sulfate fractionation, hydrophobic chromatography, affinity chromatography, ion-exchange chromatography and FPL chromatography. As those skilled in the art recognize, the determination of specific purification schemes will depend primarily on the degree of purification sought and the particular starting material used.

A preferred purification technique involves the use of a ligand capable of binnding IGPD in affinity chromatography. A preferred ligand is the compound represented by formula (II):

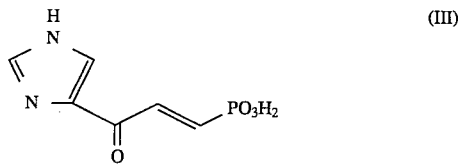

A column of a filtration gel or matrix may be prepared using standard techniques. A preferred column is prepared of thiopropyl Sepharose 6B and is then washed with 5 mM DTT in buffer A (20 mM NaPB/1 mM EDTA at pH 7.4). The ligand is applied to the column at a predetermined concentration, e.g., 60 µmol in buffer A, and the effluent is reapplied to the top of the column and recircularization is continued overnight. The column may be subsequently washed with buffer A containing 1M NaCl.

The sample from which IGPD is to be purified is added to the affinity column at a predetermined flow rate, e.g., 8 ml/hour, and the column is then washed with buffer A and then with 10 mM Tris-HCl at pH 7 before elution of the IGPD by the addition of a solution, e.g., 1M aminotriazole, which allows the desorption ofIGPD. Those skilled in the art will appreciate that specific parameters and reagents may be varied accordingly.

This embodiment of the present invention encompasses IGPD isolated from any higher plant. Preferred sottrees of lGPD include wheat, maize, rye, sorghum, flee, barley, millet, turf and forage grasses, cabbage, and pea.

In a more preferred embodiment, the IGPD is isolated from wheat germ, the preparation of which is set forth in Example 7, below. Wheat germ IGPD has a native molecular weight of from about 600,000 to about 670,000 D. The molecular weight is about 600,000 as measured by Superdex G-200 gel filtration. A molecular weight of 670,000 was determined by native PAGE. The enzyme is composed of at least 24 subunits, each with a molecular weight of 25,500. The subunits are associated non-covalently. The enzyme has a specific activity of about 5.7 U/mg of protein. The isoelectric point is about 5.65. The enzyme activity is stable up to about 30° C., but is decreased by about 50% when incubated for 40 minutes at 60° C. The enzyme remains stable, i.e. retains substantially all biological activity, when stored at −80° C. for at least one month. The Km value for wheat germ IGPD was determined as 0.4 mM. Maximal enzyme activity is at pH 6.6 as measured in 50 mM Bis-Tris-propane-HCl buffer, containing 100 mM 2-mercaptoethanol and 1 mM $MnCl_2$.

Aminotriazole, a known competitive inhibitor of *S. typhimurium* IGPD, inhibits wheat germ IGPD competitively with a Ki of about 46 gM at pH 6.6. The presence of manganese ions enhances the activity of the enzyme 7-fold at a concentration of 0.5 mM. The Km value for $Mn^{2+}$ is about 0.11. Similar to IGPD of *N. Crassa*, *S. typhimurium* and yeast, the wheat germ enzyme requires a reducing agent for activity. The wheat germ enzyme can be prepared by transforming a host cell with a DNA molecule represented by the sequence set forth in Table 3A (SEQ ID NO:9), below, consistent with the teachings of the invention.

IGPD also can be prepared via genetic engineering techniques known in the art using the IGPD cDNAs disclosed herein. In accorance with this method, a recombinant host cell stably transformed with a DNA molecule containing an IGPD structural gene, which cell is capable of expressing the gene, is cultivated under suitable conditions to allow the cell to produce IGPD in predetermined quantities, and then is isolated therefrom. The construction of chimetic DNA molecules is known in the art. The choice of specific regulatory sequences such as promoter, signal sequence, 5' and 3' untranslated sequences, and enhancer, is within the level of skill of the routineer in the art. The resultant molecule, containing the individual elements linked in proper reading frame, may be inserted into a vector capable of being transformed into the host cell. Examples include plasmids such as pBluescript (Stratagene, La Jolla, Calif.), pFLAG (International Biotechnologies, Inc., New Haven, Conn.), pTrcHis 0nvitrogen, La Jolla, Calif.), and baculovirus expression vectors, e.g., those derived from the genome of *Autogaphica californica* nuclear polyhedrosis virus (AcMNPV). A preferred baculovirus/insect system is pVl 11392/ Sf21 cells (Invitrogen, La Jolla, Calif.). Other suitable hosts include microbes, e.g., *E. coli* and yeast.

Purified IGPD may be used in assays to discover novel inhibitors of the enzyme, which inhibitors potentially would function as commercially viable herbicides. Typically, the inhibitory effect of a chemical on IGPD is determined by the absorbance difference at 370 nm using an absorbance coefficient of 10,400, which signifies the production of IAP from IGP. See, Ames et al., J. Biol. Chem. 212:687–697 (1957). Inhibitor solutions in various concentrations, e.g. 1 mM, 100 µM, 10 µM, and 1 µM, are added to the reaction mixture prior to the initiation of the enzyme reaction. A representative reaction mixture contains 50 mM Bis-Tris-propane-HCl (pH 6.6), 100 mM 2-mercaptoethanol, 1 mM $MnCl_2$, 1 mM IGP, and between 2 and 5 mU of IGPD. Once IGP is added, the reaction is rim at 30° C., and is stopped by the addition of perchlorie acid up to 10% volume of the reaction mixture. After centrifugation, the supernatant is adjusted to pH 10, e.g. by adding 1M 2-ethylaminoethanol. Alkaline phosphatase and $MgCl_2$ then are added to the mixture to final concentrations of 12 U/ml and 0.5 mM, respectively. The resultant mixture is incubated at 45° C. for 20 minutes, whereafter the mixture is chilled, e.g. in salt-ice. Five volumes of 5N NaOH are added to the solution, and after two minutes, enolized IA is measured spectroscopically. One unit of enzyme activity is defined as the amount of enzyme catalyzing the formation of 1 µmol of IAP/irnidazole acetol per minute under the assay conditions. If a measure of inhibition greater than $IC_{50}$=10 µM is expected, further assays may be performed using even lower concentrations of inhibitor.

Another embodiment of the present invention involves the use of IGPD in an assay to identify inhibitor-resistant IGPD mutants. A typical assay is as follows:

(a) incubating a first sample of IGPD and its substrate, IGP in the presence of a second sample comprising an IGPD inhibitor;

(b) measuring an unmutated activity of the IGPD from step (a);

(c) incubating a first sample of a mutated IGPD and its substrate in the presence of a second sample comprising a IGPD inhibitor;

(d) measuring a mutated activity of the mutated IGPD from step (c); and (e) comparing the mutated activity to the mutated activity of the IGPD.

The reaction mixture and the reaction conditions are the same as for the assay to identify inhibitors of IGPD (inhibitor assay) with the following modifications. First, a IGPD mutant, obtained as described above, is substituted in one of the reaction mixtures for the wild-type IGPD of the inhibitor assay. Second, an inhibitor of wild-type IGPD is present in both reaction mixtures. Third, mutated activity (enzyme activity in the presence of inhibitor and mutated IGPD) and mutated activity (enzyme activity in the presence of inhibitor and wild-type IGPD) are compared to determine whether a significant increase in enzyme activity is observed in the mutated activity when compared to the unmutated activity. Mutated activity is any measure of enzymatic activity of the mutated IGPD enzyme while in the presence of a suitable substrate and the inhibitor. Unmutated activity is any measure of enzymatic activity of the wild-type IGPD enzyme while in the presence of a suitable substrate and the inhibitor. A significant increase is defined as an increase in enzymatic activity that is larger than the margin of error inherent in the measurement technique, preferably an increase by about 2-fold of the activity of the wild-type enzyme in the presence of the inhibitor, more preferably an increase by about 5-fold, most preferably an increase greater than by about 10-fold.

The invention will be further described by reference to the following derailed examples. These examples are provided for purposes of illustration only, and are not intended to be limiting unless otherwise specified.

EXAMPLES

Example 1: Isolation of plant CDNAs that complement an *E. coil* hisB mutant

A cDNA library of polyA(+) RNA from *Arabidopsis thaliana* ecotype Columbia (Lehle Seeds, Tucson, Ariz.) was constructed in the bacteriophage vector lambda ZAP II (Stratagene Cloning Systems, La Jolla, Calif.) using the Uni-ZAP XR Gigapack II Gold cloning kit (Stratagene) as described by the manufacturer. Filamentous phagemids containing the cDNA inserts were excised from an amplified aliquot of the library using the helper phage $R_{408}$ as described in the manufacturer's instructions (Stratagene).

*Escherichia coli* strain SB3930 (CGSC#4930) was obtained from the *E. coli* Genetic Stock Center (New Haven, Conn.). SB3930 carries the hisB463 allele, which contains a specific lesion in IGPD dehydratase activity. SB3930 was rendered male by mating with *E. coli* strain K603 (CGSC

6451). K603 is auxotrophic for leucine, threonine, and tryptophan, and harbors F1::Tn10, which confers tetracycline resistance (tetR). TetR, leu+, thr+, trp+transconjugants were selected, and tested for histidine auxotrophy. The resulting strain was named ST1.

A 90 gl aliquot of the cDNA library phagemid stock ($2.1 \times 10^6$ transducing units/ml) was infected into 2.2 ml of a mid-log phase culture of strain ST1. The mixture was allowed to incubate at 37° C. for 15 minutes, then pelleted and washed in minimal Vogel-Bonner VB medium. The washed cells were plated on VB agar plates (containing ampicillin at 100 µg/ml [amp 100]) and incubated for two days at 37° C. None to several colonies were observed on each plate. Control, rich medium amp 100 plates and VB+histidine plates each had an uncountable number of colonies (greater than 10,000 colonies/plate). The negative control of ST1 without phagemid infection resulted in no colonies on (VB) amp plates.

The colonies resulting from phagemid infection were purified by repeated streaking on VB amp 100 agar. The colonies were grown in liquid culture and their plasmids extracted by methods known to those skilled in the art. The purified plasmids were tested for their ability to transform ST1 to histidine prototrophy at high frequency. Two plasmids, designated pSTA3 and pSTA4, were isolated that reproducibly complement the hisB463 mutation. The Arabidopsis cDNA encoding IGPD contained in pSTA3 is set forth in Table 1 (SEQ ID NO:1) below.

predicted amino acid sequence to the sequences of hisB from E. Coli and HIS3 from S. cerevisiae revealed a region of highly conserved sequence beginning at codon 73 of the predicted open reading frame of the cDNA. This codon was presumed to be the N terminus of mature IGPD, which was not experimentally determined because the N-terminus of the protein was blocked to Edman degradation. It was determined that the presumptive mature Arabidopsis IGP D protein sequence shares 52% identity with the gene product from E. coli and 45% identity with the HIS3 gene product from yeast, as determined using the program GAP. Deveraux et al., Nucleic Acids Res. 12, 387 (1984).

A second cDNA encoding IGPD was isolated by screening a cDNA library made from Arabidopsis leaf tissue mRNA with the IGPD cDNA probe given as Table 1. Partial sequence analysis indicated that some clones were significantly homologous to the sequence of the originally isolated IGPD within the coding region (approximately 77% identical), but contained divergent 3' non-coding sequence (approximately 50% identical), typical of cDNAs derived from independent genes. The partial clone for the second cDNA was used to screen the cDNA library, and additional clones were isolated. The partial sequence of this clone is designated as SEQ ID NO:12. The plasmid pIGPDat.2 containing this partial sequence of a second IGPD cDNA from Arabidopsis was deposited on Apr. 26, 1994 with the Agricultural Research Service, Patent Culture Collection (NRRL), Northern Regional Research Center, 1815 North

TABLE 1

(SEQ ID NO: 1)

| 1 | GTTCCTTCCG | CTGCCAACAA | AATGGAGCTG | TCGTCTGCGT | CCGCCATATT |
|---|---|---|---|---|---|
| 51 | AAGCCACTCC | TCCTCCGCCG | CTCAGCTTCT | CAGACCTAAG | CTCGGGTTTA |
| 101 | TTGATTTGCT | TCCTCGTCGA | GCGATGATCG | TTTCTTCTCC | TTCTTCTTCG |
| 151 | CTTCCTCGAT | TTTTGCGGAT | GGAATCTCAA | TCTCAGCTTC | GCCAATCTAT |
| 201 | CTCTTGCTCT | GCTTCTTCTT | CTTCTTCTAT | GGCATTAGGT | AGAATTGGAG |
| 251 | AAGTAAAGAG | AGTAACAAAG | GAAACGAATG | TTTCAGTGAA | GATTAATTTG |
| 301 | GATGGTACTG | GAGTTGCAGA | TAGTTCTAGT | GGAATTCCTT | TCCTTGACCA |
| 351 | TATGTTAGAT | CAACTTGCTT | CGCATGGCTT | GTTTGATGTG | CACGTTAGAG |
| 401 | CTACTGGTGA | TGTTCACATT | GATGATCATC | ACACTAATGA | AGATATAGCT |
| 451 | CTTGCCATTG | GAACTGCTCT | ATTAAAGGCT | CTTGGTGAGC | GTAAAGGGAT |
| 501 | TAACCGGTTT | GGTGACTTCA | CAGCTCCTCT | AGATGAAGCG | CTTATACATG |
| 551 | TTTCCTTGGA | CTTGTCTGGT | CGACCATATC | TTGGTTACAA | CTTGGAGATA |
| 601 | CCAACTCAGA | GAGTTGGAAC | ATATGATACT | CAGTTGGTGG | AGCACTTTTT |
| 651 | CCAGTCGTTG | GTGAATACTT | CTGGTATGAC | TCTTCACATT | CGGCAGCTCG |
| 701 | CTGGTGAAAA | CTCTCATCAC | ATAATAGAGG | CGACGTTTAA | GGCGTTTGCC |
| 751 | AGAGCTCTAC | GACAAGCAAC | AGAGACTGAT | CCACGCCGTG | GTGGGACAAT |
| 801 | ACCAAGTTCA | AAAGGAGTCT | TATCACGGTC | TTGAAAGCTA | ATCAAACACA |
| 851 | CAAGACAGTT | CCCAGATTCA | CACTTCATCG | TCGAGTTCAT | GAGCCATCGT |
| 901 | CAATTCTCTT | ATGGTACCAA | ATGCCAAGCC | TGTTGGATCT | TGCTGTTCCA |
| 951 | TTCCATTACA | GAAGCACAAA | GAGCAAAATG | TGAAAATAGA | TTAGAGATCA |
| 1001 | CACAGTTCAG | AAGATCATAG | GCTCATCTTT | ATATTAATCT | GTTGTTGCAG |
| 1051 | AGTGTATTAA | ACCTCTTACC | ATTGCTGTAT | CATCATCAAC | TGAGAACTTA |
| 1101 | CTGTGAGTTG | AAGTGACTGT | AATTTGCTTT | AAAAAAAAAA | |

The cDNA sequence shown in Table 1 (SEQ ID NO:1) was cloned into pBluescript, resulting in plasmid pSTA3. This plasmid is on deposit with the ATCC, 12301 Parklawn Drive, Rockville, Md. 20852. The deposit was made on Jun. 5, 1991, and accorded accession number ATCC 75014.

The Arabidopsis cDNA depicted in Table 1 (SEQ ID NO:1) is 1140 bp in length, and encodes a predicted protein of 271 amino acids, beginning with a methionine codon at nucleotide 22. The N-termius of the predicted protein has features similar to other chloroplast transit peptides, consistent with the apparent localization of the histidine biosynthetic pathway to the chloroplast. Nagai et al., Proc. Natl. Acad. Sci USA 8–8, 4133 (1991). A comparison of the University Street, Peoria, Ill. 61604, U.S.A. and was assigned accession number NRRL B-21243.

Example 2: Confirmation Of enzyme activity encoded by the plant cDNAs

Extracts of soluble protein from E. coli strains ST1 (pSTA3), ST1, and XL1-Blue (Stratagene), a wild-type his+control strain, were prepared as follows. The bacteria were grown overnight in rich medium or in the case of XL 1-Blue, in VB medium, and collected by centrifugation. Approximately 0.5–1.0 g of cells were resuspended in 4 ml of 100 mM triethanolamine (pH 7.5), 100 mM 2-mercaptoethanol, 1 mM MnCl$_2$ and broken by sonication in short pulses for 2–3 minutes. Cell debris was removed by centrifugation and proteins in the supernatant were precipitated by addition of (NH$_4$)$_2$SO$_4$ to a concentration of 80% (w/v). The protein pellet was redissolved in the buffer described above and desalted by passage over a Sephadex G-25 column (Pharmacia, Piscataway, N.J.).

IGP was synthesized as described by Ames, J. Biol. Chem. 228:131–143 (1957), and purified as follows. Charcoal was added to the acidic ehate (pH 1.0) of the Dowex 50 column, the first purification step (Ames, 1957). The clear tiltrate containing non-adsorbed IGP was neutralized with NaOH and applied on a charcoal column. Adsorbed IGP was eluted with 50% (v/v) methanol in 0.1N HCl, lyophilized and dissolved in methanol. IGP was neutralized with propylenoxide containing an equimolar amount of water.

The extracts were then assayed for IGPD activity by measuring imidazoleacetol (IA) obtained by hydrolyzing IAP as follows. The reaction mixture (total volume 125 μl) contained 50 mM Bis-Tris-propane-HCl buffer (pH 6.6), 100 mM 2-mercaptoethanol, 1 mM MnCl$_2$, 1 mM IGP, and 100 μl of bacterial extract. The reaction was started by addition of the IGP substrate, and was incubated at 37° C. and stopped after 60 minutes by adding 1/10 volume of 1N perchloric acid. After centrifugation, the supernatant was adjusted to pH 10 with 1M 2-ethylaminoethanol. Alkaline phosphatase (Sigma, St. Louis, Mo.) and MgCl$_2$ were added to the mixture to reach a final concentration of 23 mU/ml and 0.5 mM, respectively. After incubation at 45° C. for 20 minutes, the reaction mixture was chilled in a salt-ice bath. Five volumes of 5N NaOH were added to the solution, and after 2 minutes, the concentration of enolized IA was determined from the absorbance at 370 nm using the extinction coefficient of 10,400 (Ames and Mitchell, J. Biol. Chem. 212: 687–697(1955)). One unit of enzyme is defined as the amount that catalyzes the formation of 1 μmol of IAP per minute under the assay conditions described. Those skilled in the art will appreciate that reactants and reaction parameters of this assay, to the exception of alkaline phosphatase, can be varied without sacrificing sensitivity. Table 2 summarizes the data so obtained. ST1 was found to completely lack IGPD activity. XL1-Blue contained detectable IGPD activity. ST1 (pSTA3) had a comparable level of IGPD activity.

TABLE 2

| | XL1-Blue | Mutant without Activity ST1 | ST1 (pSTA3) | ST1 (pSTA4) |
|---|---|---|---|---|
| 1. +Extract +IGP | 0.197 | −0.025 | 0.21 | 0.268 |
| 2. +Extract −IGP | −0.020 | 0.002 | −0.019 | −0.016 |

TABLE 2-continued

| | XL1-Blue | Mutant without Activity ST1 | ST1 (pSTA3) | ST1 (pSTA4) |
|---|---|---|---|---|
| 3. boiled Extract +IGP | −0.007 | 0.002 | −0.015 | −0.015 |
| 4. 1-2-3 (=ΔA$_{370}$) | 0.224 | −0.029 | 0.246 | 0.299 |
| specific activity μmol/mg/h | 1.22 × 10$^{-2}$ | 0 | 1.20 × 10$^{-2}$ | 1.38 × 10$^{-2}$ |

Extracts were assayed for IGPD activity by incubation with IGP and subsequent measurement of IA as described above. Values obtained for incubation without IGP (row 2) and with boiled extracts (row 3) were subtracted from the raw values in row 1 to give the values in row 4. ST1 was found to have no activity, whereas ST1 (pSTA3) and ST1 (pSTA4) had activities comparable to XL 1-Blue.

Example 3: Isolation of an IGPD cDNA from wheat

A cDNA library was constructed as described above in Example 1 using wheat seedlings as starting material. The phage library was plated at a density of approximately 10,000 plaques on a 10 cm petri dish, and filter lifts of the plaques were made after overnight growth of the plants at 37 C. The plaque lifts were probed with the Arabidopsis cDNA, labelled with 32P-dCTP by the random priming method by means of a PrimeTime kit (International Biotechnologies, Inc., New Haven, Conn.). Hybridization conditions were 7% sodium dodecyl sulfate (SDS), 0.5M NaPO4 pH 7.0, 1 mM EDTA at 50 C. After hybridization overnight, the filters were washed with 2X SSC, 1% SDS. Positively hybridizing plaques were detected by autoradiography at a frequency of approximately one in 10,000. After purification to single plaques, cDNA inserts were excised in vivo according to manufacturer's instructions (Stratagene, La Jolla, Calif.). Plasmid DNAs were padfied using Magic Miniprep columns (Promegs Biotech, Madison, Wis.), and their sequences determined by the chain termination method using dideoxy terminators labelled with fluorescent dyes (Applied Biosystems, Inc., Foster City, Calif.). Sequences of several clones were found to share approximately 70% identity with the DNA sequence of the Arabidopsis IGPD cDNA. The sequence originally determined for one apparently full length clone is set forth below in Table 3 in the antisense, or reverse complement, orientation (SEQ ID NO:2). This sequence, with minor revisions incorporated after further sequence analysis, is set forth below in Table 3A in the sense orientation (SEQ ID NO:9).

TABLE 3

(SEQ ID NO:2)

| | | | | | |
|---|---|---|---|---|---|
| 1 | CCCCCCCTCG | AGTTTTTTTT | TTTTTTTTTT | GGAGATTATT | ATTCTATTTC |
| 51 | ATTTCACTCT | TTTGAATGGC | CAAACCATTA | TTACAGGCGC | AACACCGCGC |
| 101 | AAACCAATGC | TGAATCCATA | TATCAGAGGT | AATAACTTTC | AGAATGTCAA |
| 151 | GCCGTCTGCA | GCTTTTACAT | CTTCAGATGT | AAGTGTTGTC | CAGCAAAACT |
| 201 | GCAGTAGCGA | GCAGATACAG | TATGCCAATG | GTAGTAAGAT | AAACAAACCC |
| 251 | TGACAACAGG | ATAACAAGCA | ATTTCCATGC | TGTTCTTGTT | CCAAACCCCG |
| 301 | CGGACTGCAA | GTCCAAGTAG | CAGCAGAGAC | ATAGCAGGCG | ACCGCCCATG |

TABLE 3-continued (SEQ ID NO:2)

| | | | | |
|---|---|---|---|---|
| 351 TGTTTCTTTG | AGGGCGAATA | GCGTGCGTCC | AGTTTTCGAT | CTTGCATTGC |
| 401 AACACTAAGA | CCTTGACAGA | ACACCTTTTG | AGCTTGGCAT | AGTGCCCTGG |
| 451 CGGCGTAAGT | CATATTCCGT | TGCTTGTCGA | AGCGCCCTGG | CAAATGCTTT |
| 501 GAAGTTGCCT | CGATAATATG | GTGTGAGTTG | TTTCCCGCAA | GCTGACGGAT |
| 551 GTGAAGCGTC | ATGCCAGATG | TATTCACAAG | GGACTGGAAG | AAATGCTCAA |
| 601 CTAGCTGTGT | GTCATATGTG | CCAACTCTTT | CGGTAGGAAT | GCTTAAGCCG |
| 651 CAGCTCAAAT | GAGGTCGACC | AGATAGATCC | AGTATAACCT | CAACTGCTGC |
| 701 CTCATCAAGT | GGTGCTGTAA | AATGCCCAAA | CCGGTTAATT | CCTTTTCGGT |
| 751 CACCAAGTGC | TTGAAGTAAT | GCCGTTCCAA | TTGCTAAAGC | AATATCCTCA |
| 801 TTTGAGTGAT | GATCATCAAT | GTGTGTGTCA | CCCGTCGCCT | TCACGTATAC |
| 851 ATCAAACAGT | CCATGAGATG | CCAGTTGATC | AAGCATGTGA | TCCAAGAACG |
| 901 GTATCCCTGT | GCTGGAGTTT | GCAACACCAG | TGCCGTCCAG | GTTGATCTTG |
| 951 ACATGCACAT | TTGTTTCCTT | GGTTACCCGc | TTGACCTCCC | CCCACCCCAC |
| 1001 TTCTCCTTCT | ACGTGGAACA | ACACCTGCGG | AGGGCGCGCC | CAGGGAGCAG |
| 1051 CAGGCGCTGC | TCGAGCTTGA | GGACACCGCC | GCGCGGCTGA | GACGGGAGCG |
| 1101 GGACACGCTC | CGCAACACTC | TCAaCTACCT | TACCGCCGCG | TCTGCCGtCA |
| 1151 AGGACGTCTT | CCCCTCGTCG | CCGTCGTCGG | GGTGAAGCCT | TTCGCCTCTG |
| 1201 CCCCATCTCG | CTCGCCGATA | AGGAGTTTGT | GGAGGGTAGT | GGACTAAACC |
| 1251 TTCTTATTGC | TCTTTTTCGC | CTTTTTCCTT | TCCTTGTAAT | TGCAAGGGTA |
| 1301 GGCTTTATtT | CAATGTGGTA | GCATTTTAGC | GTGTAAAAGT | GTACGTATAA |
| 1351 TTCAGGTGTA | TTAACTCAAA | AGGAAAATGC | GGAGCTATGA | CGATGATCAA |
| 1401 TGGTAATGAT | AAGCATTTTG | CTCCAAAAAA | AAAAAAAAAA | AAACCCT |

TABLE 3A (SEQ ID NO:9)

| | | | | |
|---|---|---|---|---|
| 1 AGGGTTTTT | TTTTTTTTTT | TTTGGAGCAA | AATGCTTATC | ATTACCATTG |
| 51 ATCATCGTCA | TAGCTCCGCA | TTTTCCTTTT | GAGTTAATAC | ACCTGAATTA |
| 101 TACGTACACT | TTTACACGCT | AAAATGCTAC | CACTTGAAA | TAAAGCCTAC |
| 151 CCTTGCAATT | ACAAGGAAAG | GAAAAAGGCG | AAAAAGAGCA | ATAAGAAGGT |
| 201 TTAGTCCACT | ACCCTCCACA | AACTCCTTAT | CGGCGAGCGA | GATGGGGCAG |
| 251 AGGCGAAAGG | CTTCACCCCG | ACGACGGACA | CGAGGGGAAG | ACGTCCTTGA |
| 301 CGGCAGACGC | GGCGGTAAGG | TAGTTGAGAG | TGTTGCGGAG | CGTGTCCCGC |
| 351 TCCCGTCTCA | GCCGCGCGGC | GGTGTCCTCA | AGCTCGAGCA | GCGCCTGCTG |
| 401 CTCCCTGGGC | GCGCCCTCGA | GGTGTTGCCC | ACGTAGAAGG | AGAATGGGGT |
| 451 GGGGGGAGGT | CAAGCGGGTA | ACCAAGGAAA | CAAATGTGCA | TGTCAAGATC |
| 501 AACCTGGACG | GCACTGGTGT | TGCAAACTCC | AGCACAGGGA | TACCGTTCTT |
| 551 GGATCACATG | CTTGATCAAC | TGGCATCTCA | TGGACTGTTT | GATGTATACG |
| 601 TGAAGGCGAC | GGGTGACACA | CACATTGATG | ATCATCATC | AAATGAGGAT |
| 651 ATTGCTTTAG | CAATTGGAAC | GGCATTACTT | CAAGCACTTG | GTGACCGAAA |
| 701 AGGAATTAAC | CGGTTTGGGC | ATTTTACAGC | ACCACTTGAT | GAGGCAGCAG |
| 751 TTGAGGTTAT | ACTGGATCTA | TCTGGTCGAC | CTCATTTGAG | CTGCGGCTTA |
| 801 AGCATTCCTA | CCGAAAGAGT | TGGCACATAT | GACACACAGC | TAGTTGAGCA |
| 851 TTTCTTCCAG | TCCCTTGTGA | ATACATCTGG | CATGACGCTT | CACATCCGTC |
| 901 AGCTTGCGGG | AAACAACTCA | CACCATATTA | TCGAGGCAAC | tTTCAAAGCA |
| 951 TTTGCCAGGG | CGCTTCGACA | AGCAACGGAA | TATGACTTAC | GCCGCCAGGG |
| 1001 CACTATGCCA | AGCTCAAAAG | GTGTTCTGTC | AAGGTCTTAG | TGTTGCAATG |
| 1051 CAAGATCGAA | AACTGGACGC | ACGCTATTCG | CCCTCAAAGA | AACACATGGG |
| 1101 CGGTCGCCTG | CTATGTCTCT | GCTGCTACTT | GGACTTGCAG | TCCGCGGGGT |
| 1151 TTGGAACAAG | AACAGCATGG | AAATTGCTTG | TTATCCTGTT | GTCAGGGTTT |
| 1201 GTTTATCTTA | CTACCATTGG | CATACTGTAT | CTGCTCGCTA | CTGCAGTTTT |
| 1251 GCTGGACAAC | ACTTACATCT | GAAGATGTAA | AAGCTGCAGA | CGGCTTGACA |
| 1301 TTCTGAAAGT | TATTACCTCT | GATATATGGA | TTCAGCATTG | GTTTGCGCGG |
| 1351 TGTTGCGCCT | GTAATAATGG | TTTGGCCATT | CAAAAGAGTG | AAATGAAATA |
| 1401 GAATAATAAT | CTCCAAAAAA | AAAAAAAAAA | AACTCGAGGG | GGGG |

The cDNA sequence shown in Table 3A was cloned into the plasmid pBluscript, resulting in plasmid pWIGPD. This plasmid was deposited on Apr. 26, 1994 with the Agricultural Research Service, Patent Culture Collection (NRRL), Northern Regional Research Center, 1815 North University Street, Peoria, Ill. 61604, U.S.A. and was assigned accession number NRRLB-21242.

This example constitutes an experimental protocol with which those skilled in the art can obtain IGPD cDNAs or genes from any other higher plant species in a relatively straightforward fashion.

An alignment of the predicted amino acid sequences of the respective proteins encoded by the sequences shown in Tables 1 (from nucleotide 249 to 83 1) and 3A (from nucleotide 453 to 1037) is set forth in Table 4.

TABLE 4

```
Arab. (SEQ ID NO:3)    1 . MAL GRI GE VKR VT KE TNVS VKI NL DGT GVADS S S GI P F L DHM L DQ L A S H  49
                              ||||||||||||  |||||||||||:||. ||||||||||||||
wheat (SEQ ID NO:4)    1              GE VKR VT KE TNVHVKI NL DGT GVANS S TGI P FL DHML DQL AS H  49

50 GL F D V HVR AT GD V HI DD HHT NE DI AL AI GT AL L KAL GE R KGI NR F GDF T A   99
                         |||||.|:||||..||||||.|||||||||||||.|||:||||||||.|||
                      50 GL F D V Y V KAT GD T HI DD HHS NE DI AL AI GT AL L QAL GD R KGI NRF GHF T A  99

100 P L DE A L I HV S L DL S GR P YL GYNL E I P T Q R VGT YDT QL V EHF F QS L VNT S G  149
                         |||||  :.| |||||||.|::.|.|||:|||||||||||||||||||||
                     100 P L DE A A V E V I L DL S GR P HL S CGL S I P T E R VGT YDT QL V EHF F QS L VNT S G  149

150 MT L HI R QL AGE NS HHI I E AT F KAF AR AL R QAT E TDP R R GGT I P S S KGV L S  199
                         ||||||||||:|||||||||||||||||||||||| |  ||.||:|||||||
                     150 MT L HI R QL AGNNS HHI I E AT F KAF AR AL R QAT E YDL R R QGT MP S S KGV L S  199

200 R S  201
                         | |
                     200 R S  201
```

Identical residues are denoted by the vertical bar between the two sequences. Alignment is performed using the GAP program described in Deveraux et al., Nucleic Acids Res. 12:387–395 (1984). Regions corresponding to peptide sequences determined from the purified wheat germ IGPD (see Example 7, below) are underlined.

Example 4: Expression of recombinant IGPD in E. coli

To produce recombinant higher plant IGPD in E. coli, a translational fusion of the Arabidopsis IGPD cDNA to the 5' end of the latz gene was created in pBluescfipt SK (Stratagene, La Jolla), using the PCR overlap extension technique. Synthetic oligonucleotide primers SV124 (of sequence 5'TGC AAT CCG CGG GTA GAA TTG GAG AAG TAA 3'; SEQ ID NO:5) and SV122 (of sequence 5'GC TCC ACC AAC TGA GTA TC 3'; SEQ ID NO:6) were used in a polymerase chain reaction to amplify a DNA fragment of pSTA3 approximately 418 bp in length. The PCR product was digested at its unique SacII and XbaI sites, resulting in a fragment approximately 300 bp in length. The digestion products were separated on a low-gelling-temperature agarose gel, and the 300 bp SacII-XbaI fragment was excised. In parallel, plasmid pSTA3 was digested with SacII and XbaI, the products were separated on a gel, and the large fragment from the digestion, containing the pBluescdpt vector and 3' portion of the IGPD cDNA, was excised from the gel. This vector fragment was ligated to the 300 bp SacII-XbaI digested PCR product, and the ligation products were transformed into competent E. Coli XL1 Blue cells (Stratagene, La Jolla, Calif.).

Ampicillin resistant colonies were selected, cultured, and their plasmid DNAs extracted. The structures of the plasmids were confirmed by sequencing with the dideoxy chain termination method. A recombinant plasmid with the expected structure was designated placIGPD. The resulting fusion protein produced by this strain contained approximately 23 amino acids of the N-terminus of beta-galactosidase, followed by the presumptive mature coding sequence for Arabidopsis IGPD, which begins at codon 73 of the predicted protein coding sequence. Another plasmid for expression of higher plant IGPD in E. coli was constructed by inserting the presumptive mature coding sequence of for IGPD into the vector pFLAG (International Biotechnologies, he., New Haven, Conn.).

Example 5: Expression of recombinant IGPD in insect cells via a baculovirus expression system The IGPD cDNA was excised from pSTA3 and ligated into the baculovirus transfer vectorpVL1392 (Invitrogen Corp., San Diego, Calif.). The resulting plasmid contained the Arabidopsis IGPD coding sequence downstream of the polyhedfin promoter. The plasmid was transfected into Spodoptera frugiperda cultured cell line Sf21 (Invitrogen Corp., San Diego, Calif.), which was further transletted with wild-type AcMNPV DNA. Recombinant plaques were identified by the absence of refractile polyhedrin crystals under microscopic examination. A high titer virus stock was prepared from a single recombinant plaque. To produce recombinant IGPD, Sf21 cells (4×106/25 cm2 flask) are infected with virus at an MOI of 10. Three days after infection, the crude extract from the infected cells was assayed for IGPD activity as described above. The results are summarized in Table 5, below. The specific activity of the extract was determined to be 4.7 mU/mg, with a total activity of 6.4 mU/flask. Comparison of IGPD expression levels in Table 5 shows that Arabidopsis IGPD expressed in Tn cells gave high IGPD activity in the culture medium.

TABLE 5

Comparison of IGPD expression levels

|  | Arabidopsis IGPD (recombinant) | | E. coli*** | WheatGerm IGPD |
|---|---|---|---|---|
| Host cells | Sf21 | Tn | E. coli*** | acetone powder |
| Starting material | 1 liter culture | | | 500 g |
| Purification step | crude cell homogenate | culture medium | $(NH_4)_2SO_4$ ppt. | |
| Total activity (unit) | 1.4 | 4.0 | 0.031 | 1.5 |
| Specific activity (munit/mg protein) | 4.7* | 6.5** | 0.28 | 0.10 |

*denotes specific acitivty in cell homogenate;  denotes specific activity in the culture medium (without serum); and * denotes E. coli expressing pSTA3.

Example 6: Expression of the Arabid opsis IGPD cDNA in transgenic plants

To express the Arabidopsis protein in transgenic plants, the full length cDNA contained in pSTA3 was inserted into the plant expression vector pCGN176 1 ENX, which was derived from pCGN1761 as follows. pCGN1761 was digested at its unique EcoRI site, and ligated to a double-stranded DNA fragment comprised of two oligonucleotides of sequence 5' AAT TAT GAC GTA ACG TAG GAA TTAGCG GCCC GCT CTC GAG T 3'(SEQ ID NO:7) and 5' AAT TAC TCG AGA GCG GCC GCG AAT TCC TAC GTT ACG TCA T 3'(SEQ ID NO:8). The resulting plasmid, pCGN 176 IENX, contained unique EcoRI, NotI, and XhoI sites that lie between a duplicated 35S promoter from cauliflower mosaic virus (Kay et al., Science 236:1299–1302 (1987)) and the 3'untranslated sequences of the tml gene of Agobacterium tumefaciens. This plasmid was digested with EcoRI and XhoI, and ligated to an EcoRFXhoI fragment resulting from partial digestion of pSTA3, such that it carr/ed the complete IGPD cDNA. (The cDNA contained an internal EcoRI site). From this plasmid was excised an XbaI fragment comprising the Arabidopsis IGPD cDNA flanked by a duplicated 35S promoter and the 3' untranslated sequences of the tml gene of A. tumefaciens. This XbaI fragment was inserted into the binary vector pCIB200 at its unique XbaI site, which lies between T-DNA border sequences. The resulting plasmid, designated pCIB200IGPD, was transformed into A. tumefaciens strain CIB542. See, Uknes et al., Plant Cell 5:159–169 (1993).

Leaf disks of Nicotiana tabacum cv. Xanthi-nc were infected with A. tumefaciens CIB542 harboring pCIB200IGPD as described by Horsch et al, Science 227:1229 (1985). Kanamycin-resistant shoots from 15 independent leaf disks were transferred to rooting medium, then transplanted to soil and the resulting plants grown to maturity in the greenhouse. Seed from these plants were collected and germinated on MS agar medium containing kanamycin. Ten individual kanamycin resistant seedlings from each independent primary transformant were grown to maturity in the greenhouse, and their seed collected. These seeds were germinated on MS agar medium conta/ning kanamycin.

Plant lines that gave rise to exclusively kanamycin resistant seedlings were homozygous for the inserted gene and were subjected to further analysis. Leaf disks of each of the 15 independent transgenie lines were excised with a paper punch and placed onto MS agar containing 0 or 30 ppm of a specific IGPD inhibitor represented by formula (II), namely:

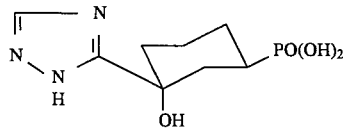

After three weeks, two sets of 10 disks from each line were weighed, and the results recorded. Transgenie lines designated IGPD-C, E, and G were approximately 3-fold more resistant to the inhibitor than wild type, non-transformed plants.

RNA was extracted from leaves of each of these lines. Total RNA from each independent homozygous line, and from non-transgenic control plants, was separated by agarose gel electrophoresis in the presence of formaldehyde (Ausubel et al., Current ProtoCols in Molecular Biology, Wiley & Sons, New York (1987)). The gel was blotted to nylon membrane (Ausubel et al., supra.) and hybridized with the radiolabelled Arabidopsis IGPD cDNA. Hybridization and washing conditions were as described by Church and Gilbert, Proc. Natl. Acad. Sei. USA 81:1991–1995 (1984). The filter was autoradiographed, and intense RNA bands corresponding to the IGPD transgene were detected in all four transgenie plant lines.

Seeds of the IGPD-G line displaying the highest apparent level of Arabidopsis IGPD message were tested for resistance to the specific IGPD inhibitor represented by formula (I). Seeds from the transgenie line and from wild type non-transformed tobacco were germinated on MS agar medium containing the inhibitor at concentrations of 1500 and 3000 ppm. growth of the seedlings was visually scored after two weeks. The results are set forth below in Table 6.

TABLE 6

| ppm | 0 | 1500 | 3000 |
|---|---|---|---|
| Xanthi | +++ | + | + |
| IGPD-G (IGPD over expression) | +++ | +++ | ++ |

+ denotes severe inhibition of growth phenotype;
++ denotes slight inhibition of growth phenotype
+++ denotes no inhibition of growth phenotype The table summarizes visually obtained data concerning seedling growth on the IGPD inhibitor of formula (i). Seedlings of line IGPD-G showed uninhibited growth when germinated on MS medium containing 1,500 ppm IGPD inhibitor of formula (I). At 3,000 ppm, there was only slight inhibition of growth. Wild-type tobacco plants were inhibited on medium containing 1,500 and 3,000 ppm inhibitor of formula (I).

Leaves from these homozygous transgenie plants were collected, frozen in liquid nitrogen, and homogenized in 200 mM triethanolamine-HCl, 10% Polyclar AT (WAKO Pure Chemical Co., Osaka, Japan). The extract was filtered through Miracloth (Calbiochem, San lo Diego, Calif.), and assayed for IGPD activity as described in Example 7. The activity was determined to be 0.68 mU/mg protein, or 7.45 mU/g fresh weight. This compared favorably to the undetectable level of activity in non-transgenic control tobacco plants, either in a crude extract, or a 30–60% ammonium sulfate fraction. IGPD activities in other plant species are summarized in Table 7.

TABLE 7

| Plant Source | Specific Activity (mU/mg[a]) | Extractable activity (mU/g)[b] |
|---|---|---|
| Tobacco leaves | 0 | 0 |
| Transgenic tobacco leaves (IGPD-G) | 0.68 | 7.45 |
| Barley shoots (Hordeum vulgare L) | 0.25 | 0.95 |
| Cabbage shoots (Brassica oleracea L.) | 0.13 | 0.22 |
| Cucumber shoots (Cucumis sativus L.) | 0 | 0 |
| Lettuce shoots (Lactuca sativa L.) | 0 | 0 |
| Maize shoots (Zea mays L.) | 0.06 | 0.27 |
| Oats shoots (Avena sativa L.) | 0 | 0 |
| Pea shoots (Pisum sativum L.) | 0.09 | 0.61 |
| Rice germ | 0.03 | 0.73 |
| Wheat germ | 0.05 | 3.20 |
| Rose cell culture (Rosa "Paul's" Scarlet) | 0.23 | 0.04 |

[a]Units of acitivity per milligram of protein.
[b]Units of activity per gram of plant material.

These results indicate that the activity of IGPD in the crude extract of transgenie tobacco plants exceeds the activity of IGPD in the 80% ammonium sulfate fraction from any plant species tested.

To further evaluate resistance of the IGPD-overexpressing line IGPD-G, plants were grown in the greenhouse and treated with various concentrations of the inhibitor IRL 1803. After treatment, plants were photographed, and their health was visually scored. The results are recorded in Table 8, below.

TABLE 8

| [IRL 1803](ppm) | Visual Score after Treatment | |
| --- | --- | --- |
| | Xanthi (untransformed) | IGPD-G |
| 0 | 5 | 5 |
| 1000 | 3 | 4 |
| 10000 | 1 | 2 |

1 = severe stunting, severe chlorosis combined with necrosis
2 = severe stunting, some interveinal chlorosis
3 = moderate stunting, some interveinal chlorosis, pinnate leaves
4 = moderate stunting, normal leaf morphology
5 = healthy, with no symptoms Example 7: Purification Of IGPD from wheat germ Wheat germ (Sigma Chemical Co., St. Louis) was processed into an acetone powder. The following steps were carded out at 4° C. The acetone powder was suspended in 200 mM triethanolamine-HCl (TEA-HCl) and the insoluble material removed from the tiltrate by centrifugation. The supernatant was precipitated with ammonium sulfate (30% saturation) and centrifuged. The supernatant was loaded onto a Butyl-Toyopearl 650M column equilibrated with 50 mM TEA-HCl (pH 7.5) containing 1 mM $MgCl_2$, 100 mM 2-mercaptoethanol, and ammonium sulfate (20% saturation). Enzyme activity was eluted with a linear gradient of sulfate (80% saturation) and dissolved in 20 mM TEA-HCl (pH 7.5) containing 1 mM $MnCl_2$ and 100 mM 2-mercaptoethanol (purification buffer). After desalting on Sephadex G-25, the extract was loaded onto a DEAE-Toyopearl 650M column equilibrated with purification buffer. The enzyme was eluted with a linear gradient of NaCl (0–500 mM) in purification buffer. The active fractions were desalted on Sephadex G-25 and subjected to MonoQ FPLC (Pharmacia-LKB) using purification buffer. The active fractions were pooled and concentrated by ultrafiltration (Amicon YM30). This preparation was chromatographed twice on Superalex 200 FPLC (Pharmacia-LKB) using purification buffer containing 150 mM NaCl. The obtained enzyme preparation was storm at −80° C. until used.

Table 9 summarizes the purification of IGPD from wheat germ leading to a 114,000-fold purification of the enzyme.

Determination Of IGPD activity

IGPD activity was determined by measuring imidazoleacetol obtained by hydrolyzing IAP. The dehydratase reaction mixture contained 50 mM Bis-Tfis-propane-HCl buffer (pH 6.6), 100 mM 2-mercaptoethanol, 1 mM $MnCl_2$, 1 mN IGP, and 2 to 5 mU of enzyme in a volume of 0.25 ml. The reaction was started by the addition of substrate, incubated at 30° C. and stopped after 40 minutes by adding 10% (v/v) of 1N pertbiotic acid. After centrifugation, the supernatant was adjusted to pH 10 by 1M 2-ethylaminoethanol. Alkaline phosphatase and $MgCl_2$ were added to the mixture to reach a final concentration of 23 mU/.L and 0.5 mM, respectively. After incubation at 45° C. for 20 min, the reaction mixture was chilled in salt-ice. Five volumes of 5N NaOH were added to the solution, and after 2 minutes, the concentration of enolized imidazoleacetol was determined from the absorbance at 370 nm using the absorbance coefficient of 10,400 (Ames and Mitchell, 1955). One unit of enzyme activity was defined as the amount of enzyme catalyzing the formation of 1 μmol of IAP/imidazoleacetol per minute under the assay conditions.

Determination of histidinol phosphatase activity

Histidinol phosphatase activity was determined by measuring the formation of inorganic phosphate according to the method described earlier (Ames et al. 1960) with some modifications. The assay mixture contained 200 mM TEA-HCl (pH 8.2), 5 mM L-histidinol phosphate, and enzyme in a final volume of 180 μL. The reaction was started with the addition of substrate, incubated at 37° C. for 180 minutes and stopped with 10% (v/v) of 1N perchloric acid. The mixture was centrifuged at 10,000 rpm for 3 min. An aliquot of 180 μl of the supernatant was mixed with 420 μL of the ascorbate-molybdate reagent and incubated at 45° C. for 20 min. The absorption was read at 820 nm against a control without substrate or enzyme. One unit of enzyme activity was defined as the amount of enzyme catalyzing the formation of 1 μmol of phosphate per minute under the assay conditions.

Protein determination

The protein concentration was determined by the Bradford protein assay method using bovine serum albumin as a standard (Bradford, 1976).

TABLE 9

Purification of IGPD from wheat germ

| Purification step | Total protein (mg) | Total activity (mU) | Recovery (%) | Specific activity (mU/mg) | Purification (fold) |
| --- | --- | --- | --- | --- | --- |
| $(NH_4)_2SO_4$ fractionation | 128,000 | 6400 | 100 | 0.05 | 1 |
| Butyl-Toyo-pearlhydro-phobicchroma-tography | 5,600 | 4,870 | 76 | 0.87 | 17 |
| DEAE-Toyopearl-ionexchange chromatography | 565 | 1,040 | 16 | 1.8 | 36 |
| MonoQFPLC | 25.3 | 652 | 10 | 25.8 | 516 |
| Superdex200FPLC (runtwice) | 0.035 | 199 | 3 | 5700 | 114,000 |

Electrophoresis

SDS-PAGE was carded out according to Laemnli (1970) using a gradient gel (Phastgel 8–25, Pharmacia-LKB). Native PAGE was done as described (Davis 1964) using a slab gradient gel (PAG plate 4/15, Dai-ichi Chemicals, Japan). Isoelectric focusing was carried out using a polyacrylamide gel (4%) with Selvalyt pH 3–7 as the carder ampholyte. The pI value was calculated using a calibration kit (Pharmacia-LKB).

The purified IGPD so obtained was digested with lysyl endopeptidase, and the resulting digest was separated by reverse phase HPLC. The resulting peptides were subjected to automated Edman degradation (Strickler et al., Anal. Biochem. 140:553–566 (1984)) with an Applied Biosystems froster City, Calif.) 470A protein sequencer. The following peptide sequences were determined:

Peptide#1 GINRFGHFTAPLDEA (SEQ ID NO:10)

Peptide #2 GVLSRV (SEQ ID NO:11)

Peptide #1 exactly matched the predicted protein sequence determined from the wheat IGPD cDNA (Table 4, underlined). Peptide #2 differed from the predicted protein sequence derived from the cDNA at the last residue. The discrepancy compared to the amino acid sequence of the peptide was likely due to the presence of multiple isoforms encoded by different genes in the wheat genome, especially given the fact that Arabidopsis has two IGPD genes as determined by genomic Southern blot. Wheat, with its hexaploid genome, may have even more than two IGPD genes. Furthermore, these sequences were nearly identical to two segments of the predicted protein sequence encoded by the Arabidopsis IGPD cDNA (Table 4).

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Various modifications of the invention described herein will become apparent to those skilled in the art. Such modifications are intended to fall within the scope of the appended claims.

---

We claim:

1. A purified DNA molecule encoding a higher plant imidazoleglycerol phosphate dehydratas (IGPD).

2. A DNA molecule of claim 1, wherein said higher plant is wheat.

3. The DNA molecule of claim 2 comprising the sequence set forth in SEQ ID NO:9.

4. A DNA molecule of claim 1, wherein said higher plant is Arabidopsis.

5. The DNA molecule of claim 4 comprising the sequence set forth in SEQ ID NO:1.

6. A recombinant DNA molecule, comprising a promoter capable of driving expression of an associated coding sequence in a host cell, operably linked to a molecule encoding a higher plant IGPD.

7. A recombinant vector, comprising a DNA molecule of claim 6, wherein said vector is capable of being stably transformed into a host cell 8. A hot cell stably transformed with a vector of claim 7, wherein said host cell is capable of expressing IGPD.

9. A hot cell of claim 8, which is a lant cell, a bacterial cell, or an insect cell.

10. The recombinant DNA molecule of claim 6 wherein said host cell is selected from the group consisting of a plant cell, a bacterial cell and an insect cell.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1140 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Arabidopsis thaliana ( i x ) FEATURE:
        ( A ) NAME/KEY: misc_feature
        ( B ) LOCATION: 1..1140
        ( C ) IDENTIFICATION METHOD: experimental
        ( D ) OTHER INFORMATION: /evidence=EXPERIMENTAL
            / note="Arabidopsis cDNA encoding IGPD contained
            in pSTA3"

( x i ) SEQUENCE DESCRIPTION: SEQ ID NO:1:

```
GTTCCTTCCG  CTGCCAACAA  AATGGAGCTG  TCGTCTGCGT  CCGCCATATT  AAGCCACTCC      60

TCCTCCGCCG  CTCAGCTTCT  CAGACCTAAG  CTCGGGTTTA  TTGATTTGCT  TCCTCGTCGA     120

GCGATGATCG  TTTCTTCTCC  TTCTTCTTCG  CTTCCTCGAT  TTTTGCGGAT  GGAATCTCAA     180

TCTCAGCTTC  GCCAATCTAT  CTCTTGCTCT  GCTTCTTCTT  CTTCTTCTAT  GGCATTAGGT     240

AGAATTGGAG  AAGTAAAGAG  AGTAACAAAG  GAAACGAATG  TTTCAGTGAA  GATTAATTTG     300

GATGGTACTG  GAGTTGCAGA  TAGTTCTAGT  GGAATTCCTT  TCCTTGACCA  TATGTTAGAT     360

CAACTTGCTT  CGCATGGCTT  GTTTGATGTG  CACGTTAGAG  CTACTGGTGA  TGTTCACATT     420
```

```
GATGATCATC  ACACTAATGA  AGATATAGCT  CTTGCCATTG  GAACTGCTCT  ATTAAAGGCT    480

CTTGGTGAGC  GTAAAGGGAT  TAACCGGTTT  GGTGACTTCA  CAGCTCCTCT  AGATGAAGCG    540

CTTATACATG  TTTCCTTGGA  CTTGTCTGGT  CGACCATATC  TTGGTTACAA  CTTGGAGATA    600

CCAACTCAGA  GAGTTGGAAC  ATATGATACT  CAGTTGGTGG  AGCACTTTTT  CCAGTCGTTG    660

GTGAATACTT  CTGGTATGAC  TCTTCACATT  CGGCAGCTCG  CTGGTGAAAA  CTCTCATCAC    720

ATAATAGAGG  CGACGTTTAA  GGCGTTTGCC  AGAGCTCTAC  GACAAGCAAC  AGAGACTGAT    780

CCACGCCGTG  GTGGGACAAT  ACCAAGTTCA  AAAGGAGTCT  TATCACGGTC  TTGAAAGCTA    840

ATCAAACACA  CAAGACAGTT  CCCAGATTCA  CACTTCATCG  TCGAGTTCAT  GAGCCATCGT    900

CAATTCTCTT  ATGGTACCAA  ATGCCAAGCC  TGTTGGATCT  TGCTGTTCCA  TTCCATTACA    960

GAAGCACAAA  GAGCAAAATG  TGAAATAGA   TTAGAGATCA  CACAGTTCAG  AAGATCATAG   1020

GCTCATCTTT  ATATTAATCT  GTTGTTGCAG  AGTGTATTAA  ACCTCTTACC  ATTGCTGTAT   1080

CATCATCAAC  TGAGAACTTA  CTGTGAGTTG  AAGTGACTGT  AATTTGCTTT  AAAAAAAAAA   1140
```

( 2 ) INFORMATION FOR SEQ ID NO:2:

( i ) SEQUENCE CHARACTERISTICS:
        ( A ) LENGTH: 1447 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v i ) ORIGINAL SOURCE:
        ( A ) ORGANISM: Triticum aestivum ( i x ) FEATURE:
        ( A ) NAME/KEY: misc_feature
        ( B ) LOCATION: 1..1447
        ( C ) IDENTIFICATION METHOD: experimental
        ( D ) OTHER INFORMATION: /evidence=EXPERIMENTAL
            / note="full length cDNA clone of IGPD from wheat"

( x i ) SEQUENCE DESCRIPTION: SEQ ID NO:2:

```
CCCCCCCTCG  AGTTTTTTTT  TTTTTTTTT   GGAGATTATT  ATTCTATTTC  ATTTCACTCT     60

TTTGAATGGC  CAAACCATTA  TTACAGGCGC  AACACCGCGC  AAACCAATGC  TGAATCCATA    120

TATCAGAGGT  AATAACTTTC  AGAATGTCAA  GCCGTCTGCA  GCTTTTACAT  CTTCAGATGT    180

AAGTGTTGTC  CAGCAAAACT  GCAGTAGCGA  GCAGATACAG  TATGCCAATG  GTAGTAAGAT    240

AAACAAACCC  TGACAACAGG  ATAACAAGCA  ATTTCCATGC  TGTTCTTGTT  CCAAACCCCG    300

CGGACTGCAA  GTCCAAGTAG  CAGCAGAGAC  ATAGCAGGCG  ACCGCCCATG  TGTTTCTTTG    360

AGGGCGAATA  GCGTGCGTCC  AGTTTCGAT   CTTGCATTGC  AACACTAAGA  CCTTGACAGA    420

ACACCTTTTG  AGCTTGGCAT  AGTGCCCTGG  CGGCGTAAGT  CATATTCCGT  TGCTTGTCGA    480

AGCGCCCTGG  CAAATGCTTT  GAAGTTGCCT  CGATAATATG  GTGTGAGTTG  TTTCCCGCAA    540

GCTGACGGAT  GTGAAGCGTC  ATGCCAGATG  TATTCACAAG  GGACTGGAAG  AAATGCTCAA    600

CTAGCTGTGT  GTCATATGTG  CCAACTCTTT  CGGTAGGAAT  GCTTAAGCCG  CAGCTCAAAT    660

GAGGTCGACC  AGATAGATCC  AGTATAACCT  CAACTGCTGC  CTCATCAAGT  GGTGCTGTAA    720

AATGCCCAAA  CCGGTTAATT  CCTTTCGGT   CACCAAGTGC  TTGAAGTAAT  GCCGTTCCAA    780

TTGCTAAAGC  AATATCCTCA  TTTGAGTGAT  GATCATCAAT  GTGTGTGTCA  CCCGTCGCCT    840

TCACGTATAC  ATCAAACAGT  CCATGAGATG  CCAGTTGATC  AAGCATGTGA  TCCAAGAACG    900
```

```
GTATCCCTGT GCTGGAGTTT GCAACACCAG TGCCGTCCAG GTTGATCTTG ACATGCACAT      960
TTGTTTCCTT GGTTACCCGC TTGACCTCCC CCCACCCCAC TTCTCCTTCT ACGTGGAACA     1020
ACACCTGCGG AGGGCGCGCC CAGGGAGCAG CAGGCGCTGC TCGAGCTTGA GGACACCGCC     1080
GCGCGGCTGA GACGGGAGCG GGACACGCTC CGCAACACTC TCAACTACCT TACCGCCGCG     1140
TCTGCCGTCA AGGACGTCTT CCCCTCGTCG CCGTCGTCGG GGTGAAGCCT TCGCCTCTG      1200
CCCCATCTCG CTCGCCGATA AGGAGTTTGT GGAGGGTAGT GGACTAAACC TTCTTATTGC     1260
TCTTTTTCGC CTTTTTCCTT TCCTTGTAAT TGCAAGGGTA GGCTTTATTT CAATGTGGTA     1320
GCATTTTAGC GTGTAAAAGT GTACGTATAA TTCAGGTGTA TTAACTCAAA AGGAAAATGC     1380
GGAGCTATGA CGATGATCAA TGGTAATGAT AAGCATTTTG CTCCAAAAAA AAAAAAAAA      1440
AAACCCT                                                               1447
```

(2) INFORMATION FOR SEQ ID NO:3:

(i) SEQUENCE CHARACTERISTICS:
        (A) LENGTH: 201 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (ix) FEATURE:
        (A) NAME/KEY: Protein
        (B) LOCATION: 1..201
        (D) OTHER INFORMATION: /note="predicted amino acid
        sequence of IGPD derived from SEQ ID NO:1"

(xi) SEQUENCE DESCRIPTION: SEQ ID NO:3:

```
Met Ala Leu Gly Arg Ile Gly Glu Val Lys Arg Val Thr Lys Glu Thr
 1               5                  10                  15

Asn Val Ser Val Lys Ile Asn Leu Asp Gly Thr Gly Val Ala Asp Ser
             20                  25                  30

Ser Ser Gly Ile Pro Phe Leu Asp His Met Leu Asp Gln Leu Ala Ser
         35                  40                  45

His Gly Leu Phe Asp Val His Val Arg Ala Thr Gly Asp Val His Ile
     50                  55                  60

Asp Asp His His Thr Asn Glu Asp Ile Ala Leu Ala Ile Gly Thr Ala
 65                  70                  75                  80

Leu Leu Lys Ala Leu Gly Glu Arg Lys Gly Ile Asn Arg Phe Gly Asp
                 85                  90                  95

Phe Thr Ala Pro Leu Asp Glu Ala Leu Ile His Val Ser Leu Asp Leu
                100                 105                 110

Ser Gly Arg Pro Tyr Leu Gly Tyr Asn Leu Glu Ile Pro Thr Gln Arg
            115                 120                 125

Val Gly Thr Tyr Asp Thr Gln Leu Val Glu His Phe Phe Gln Ser Leu
        130                 135                 140

Val Asn Thr Ser Gly Met Thr Leu His Ile Arg Gln Leu Ala Gly Glu
145                 150                 155                 160

Asn Ser His His Ile Ile Glu Ala Thr Phe Lys Ala Phe Ala Arg Ala
                165                 170                 175

Leu Arg Gln Ala Thr Glu Thr Asp Pro Arg Arg Gly Gly Thr Ile Pro
            180                 185                 190
```

Ser  Ser  Lys  Gly  Val  Leu  Ser  Arg  Ser
          195                 200

( 2 ) INFORMATION FOR SEQ ID NO:4:

( i ) SEQUENCE CHARACTERISTICS:
        ( A ) LENGTH: 195 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( i x ) FEATURE:
        ( A ) NAME/KEY: Protein
        ( B ) LOCATION: 1..195
        ( D ) OTHER INFORMATION: /note="predicted amino acid
            sequence derived from SEQ ID NO:9"

( x i ) SEQUENCE DESCRIPTION: SEQ ID NO:4:

Gly  Glu  Val  Lys  Arg  Val  Thr  Lys  Glu  Thr  Asn  Val  His  Val  Lys  Ile
 1                    5                   10                           15

Asn  Leu  Asp  Gly  Thr  Gly  Val  Ala  Asn  Ser  Ser  Thr  Gly  Ile  Pro  Phe
               20                    25                        30

Leu  Asp  His  Met  Leu  Asp  Gln  Leu  Ala  Ser  His  Gly  Leu  Phe  Asp  Val
          35                    40                        45

Tyr  Val  Lys  Ala  Thr  Gly  Asp  Thr  His  Ile  Asp  Asp  His  His  Ser  Asn
     50                    55                         60

Glu  Asp  Ile  Ala  Leu  Ala  Ile  Gly  Thr  Ala  Leu  Leu  Gln  Ala  Leu  Gly
65                        70                    75                         80

Asp  Arg  Lys  Gly  Ile  Asn  Arg  Phe  Gly  His  Phe  Thr  Ala  Pro  Leu  Asp
                    85                         90                         95

Glu  Ala  Ala  Val  Glu  Val  Ile  Leu  Asp  Leu  Ser  Gly  Arg  Pro  His  Leu
               100                   105                       110

Ser  Cys  Gly  Leu  Ser  Ile  Pro  Thr  Glu  Arg  Val  Gly  Thr  Tyr  Asp  Thr
          115                   120                       125

Gln  Leu  Val  Glu  His  Phe  Phe  Gln  Ser  Leu  Val  Asn  Thr  Ser  Gly  Met
     130                        135                   140

Thr  Leu  His  Ile  Arg  Gln  Leu  Ala  Gly  Asn  Asn  Ser  His  His  Ile  Ile
145                        150                   155                      160

Glu  Ala  Thr  Phe  Lys  Ala  Phe  Ala  Arg  Ala  Leu  Arg  Gln  Ala  Thr  Glu
                    165                   170                       175

Tyr  Asp  Leu  Arg  Arg  Gln  Gly  Thr  Met  Pro  Ser  Ser  Lys  Gly  Val  Leu
               180                   185                       190

Ser  Arg  Ser
          195

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: PCR primer SV124 used to amplify fragment
            from pSTA3

( i i i ) HYPOTHETICAL: NO ( i v ) ANTI-SENSE: NO ( x i ) SEQUENCE DESCRIPTION: SEQ ID NO:5:

TGCAATCCGC GGGTAGAATT GGAGAAGTAA 30

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: PCR primer SV122 used to amplify fragment
            from pSTA3

( i i i ) HYPOTHETICAL: NO ( i v ) ANTI-SENSE: NO ( x i ) SEQUENCE DESCRIPTION: SEQ ID NO:6:

TGCTCCACCA ACTGAGTATC 20

( 2 ) INFORMATION FOR SEQ ID NO:7:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide used to create pCGN1761ENX ( i i i ) HYPOTHETICAL: NO ( i v ) ANTI-SENSE: NO ( x i ) SEQUENCE DESCRIPTION: SEQ ID NO:7:

AATTATGACG TAACGTAGGA ATTAGCGGCC CGCTCTCGAG T 41

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: Oligonucleotide used to create pCGN1761ENX ( i i i ) HYPOTHETICAL: NO ( i v ) ANTI-SENSE: NO ( x i ) SEQUENCE DESCRIPTION: SEQ ID NO:8:

AATTACTCGA GAGCGGCCGC GAATTCCTAC GTTACGTCAT 40

( 2 ) INFORMATION FOR SEQ ID NO:9:

( i ) SEQUENCE CHARACTERISTICS:
        ( A ) LENGTH: 1444 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: misc_feature
    ( B ) LOCATION: 1..1444
    ( D ) OTHER INFORMATION: /note="apparent full length cDNA clone of wheat IGPD; protein sequence in SEQ ID NO:4"

( i x ) FEATURE:
    ( A ) NAME/KEY: CDS
    ( B ) LOCATION: 453..1037
    ( D ) OTHER INFORMATION: /product="mature IGPD from wheat"

( x i ) SEQUENCE DESCRIPTION: SEQ ID NO:9:

```
AGGGTTTTTT TTTTTTTTTT TTTGGAGCAA AATGCTTATC ATTACCATTG ATCATCGTCA        60

TAGCTCCGCA TTTTCCTTTT GAGTTAATAC ACCTGAATTA TACGTACACT TTTACACGCT       120

AAAATGCTAC CACATTGAAA TAAAGCCTAC CCTTGCAATT ACAAGGAAAG GAAAAAGGCG       180

AAAAAGAGCA ATAAGAAGGT TTAGTCCACT ACCCTCCACA AACTCCTTAT CGGCGAGCGA       240

GATGGGGCAG AGGCGAAAGG CTTCACCCCG ACGACGGCGA CGAGGGGAAG ACGTCCTTGA       300

CGGCAGACGC GGCGGTAAGG TAGTTGAGAG TGTTGCGGAG CGTGTCCCGC TCCCGTCTCA       360

GCCGCGCGGC GGTGTCCTCA AGCTCGAGCA GCGCCTGCTG CTCCCTGGGC GCGCCCTCGA       420

GGTGTTGCCC ACGTAGAAGG AGAATGGGGT GG GGG GAG GTC AAG CGG GTA ACC        473
                                   Gly Glu Val Lys Arg Val Thr
                                    1               5

AAG GAA ACA AAT GTG CAT GTC AAG ATC AAC CTG GAC GGC ACT GGT GTT        521
Lys Glu Thr Asn Val His Val Lys Ile Asn Leu Asp Gly Thr Gly Val
         10              15                  20

GCA AAC TCC AGC ACA GGG ATA CCG TTC TTG GAT CAC ATG CTT GAT CAA        569
Ala Asn Ser Ser Thr Gly Ile Pro Phe Leu Asp His Met Leu Asp Gln
     25              30                  35

CTG GCA TCT CAT GGA CTG TTT GAT GTA TAC GTG AAG GCG ACG GGT GAC        617
Leu Ala Ser His Gly Leu Phe Asp Val Tyr Val Lys Ala Thr Gly Asp
 40              45                  50                      55

ACA CAC ATT GAT GAT CAT CAC TCA AAT GAG GAT ATT GCT TTA GCA ATT        665
Thr His Ile Asp Asp His His Ser Asn Glu Asp Ile Ala Leu Ala Ile
                 60              65                  70

GGA ACG GCA TTA CTT CAA GCA CTT GGT GAC CGA AAA GGA ATT AAC CGG        713
Gly Thr Ala Leu Leu Gln Ala Leu Gly Asp Arg Lys Gly Ile Asn Arg
             75                  80                  85

TTT GGG CAT TTT ACA GCA CCA CTT GAT GAG GCA GCA GTT GAG GTT ATA        761
Phe Gly His Phe Thr Ala Pro Leu Asp Glu Ala Ala Val Glu Val Ile
         90                  95                 100

CTG GAT CTA TCT GGT CGA CCT CAT TTG AGC TGC GGC TTA AGC ATT CCT        809
Leu Asp Leu Ser Gly Arg Pro His Leu Ser Cys Gly Leu Ser Ile Pro
105                 110                 115

ACC GAA AGA GTT GGC ACA TAT GAC ACA CAG CTA GTT GAG CAT TTC TTC        857
Thr Glu Arg Val Gly Thr Tyr Asp Thr Gln Leu Val Glu His Phe Phe
120                 125                 130                 135

CAG TCC CTT GTG AAT ACA TCT GGC ATG ACG CTT CAC ATC CGT CAG CTT        905
Gln Ser Leu Val Asn Thr Ser Gly Met Thr Leu His Ile Arg Gln Leu
             140                 145                 150

GCG GGA AAC AAC TCA CAC CAT ATT ATC GAG GCA ACT TTC AAA GCA TTT        953
Ala Gly Asn Asn Ser His His Ile Ile Glu Ala Thr Phe Lys Ala Phe
         155                 160                 165

GCC AGG GCG CTT CGA CAA GCA ACG GAA TAT GAC TTA CGC CGC CAG GGC       1001
Ala Arg Ala Leu Arg Gln Ala Thr Glu Tyr Asp Leu Arg Arg Gln Gly
     170                 175                 180

ACT ATG CCA AGC TCA AAA GGT GTT CTG TCA AGG TCT TAGTGTTGCA            1047
Thr Met Pro Ser Ser Lys Gly Val Leu Ser Arg Ser
185                 190                 195
```

| ATGCAAGATC | GAAAACTGGA | CGCACGCTAT | TCGCCCTCAA | AGAAACACAT | GGGCGGTCGC | 1107 |
| CTGCTATGTC | TCTGCTGCTA | CTTGGACTTG | CAGTCCGCGG | GGTTTGGAAC | AAGAACAGCA | 1167 |
| TGGAAATTGC | TTGTTATCCT | GTTGTCAGGG | TTTGTTTATC | TTACTACCAT | TGGCATACTG | 1227 |
| TATCTGCTCG | CTACTGCAGT | TTTGCTGGAC | AACACTTACA | TCTGAAGATG | TAAAAGCTGC | 1287 |
| AGACGGCTTG | ACATTCTGAA | AGTTATTACC | TCTGATATAT | GGATTCAGCA | TTGGTTTGCG | 1347 |
| CGGTGTTGCG | CCTGTAATAA | TGGTTTGGCC | ATTCAAAAGA | GTGAAATGAA | ATAGAATAAT | 1407 |
| AATCTCCAAA | AAAAAAAAA | AAAAACTCGA | GGGGGGG | | | 1444 |

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Peptide
        ( B ) LOCATION: 1..15
        ( D ) OTHER INFORMATION: /note="Sequence for internal
            peptide #1 of purified IGPD"

( x i ) SEQUENCE DESCRIPTION: SEQ ID NO:10:

Gly Ile Asn Arg Phe Gly His Phe Thr Ala Pro Leu Asp Glu Ala
1               5                   10                  15

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Peptide
        ( B ) LOCATION: 1..6
        ( D ) OTHER INFORMATION: /note="Sequence for internal
            peptide #2 of purified IGPD"

( x i ) SEQUENCE DESCRIPTION: SEQ ID NO:11:

Gly Val Leu Ser Arg Val
1               5

( 2 ) INFORMATION FOR SEQ ID NO:12:

( i ) SEQUENCE CHARACTERISTICS:
        ( A ) LENGTH: 787 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Arabidopsis thaliana ( v i i ) IMMEDIATE SOURCE:
    ( B ) CLONE: pIGPDat.2

( x i ) SEQUENCE DESCRIPTION: SEQ ID NO:12:

```
GGCACGAGGA  TCAACTTGCT  TCACATGGCT  TGTTCGATGT  ACACGTAAGA  GCTACTGGTG    60
ATACTCACAT  TGATGATCAT  CATACTAATG  AAGATGTTGC  TCTTGCCATT  GGAACTGCTT   120
TGTTAAAGGC  ACTTGGGGAA  CGGAAAGGGA  TTAATCGTTT  TGGCGATTTT  ACAGCTCCTC   180
TTGATGAAGC  ACTCATACAT  GTTTCCCTGG  ATCTATCTGG  TAGACCATAT  CTTGGATACA   240
ACTTAGAGAT  TCCAACGCAG  AGAGTAGGAA  CATACGACAC  TCAGTTGGTG  GAACACTTCT   300
TCCAGTCATT  GGTGAATACT  TCTGGTATGA  CTCTTCACAT  CCGACAGCTT  GCTGGTAAAA   360
ACTCGCATCA  CATAATAGAA  GCGACCTTTA  AGGCCTTTGC  AAGAGCTCTC  CGACAAGCAA   420
CAGAGTCTGA  TCCACGCCGC  GGTGGGACAA  TACCAAGCTC  GAAAGGAGTC  TTGTCACGTT   480
CATAAGAGGA  CTTGATGAGC  ATGGGTCAGT  TGTCTGAATG  TCTTATGTAC  AATGTCAAAC   540
ATGCTGGATC  TTTGTTCATT  TGCAAAGGTC  AATGTATCTA  ATCTAGCTAA  TTGATTATTG   600
TTGGTCACCA  GGATCTTTTT  GCTCTCTCTA  GTTCTAGACT  TTGTTCACCT  TAAGCCAGAG   660
CTCTTTAATC  AGGAGTTACT  CGTAATCATT  TTGTTTTGGT  CATGTGTGCA  CCATTTACGA   720
GTGTCATGCT  CGTGATTCAT  GGAGCTTTAC  TCTGTATTGT  TTGTCCAAAA  AAAAAAAAA    780
AAAAAAA                                                                  787
```